(12) United States Patent
Pan-Montojo

(10) Patent No.: US 11,426,372 B2
(45) Date of Patent: Aug. 30, 2022

(54) GLYCOLIC ACID PROTECTS AGAINST ISCHEMIC INSULTS

(71) Applicant: Francisco Pan-Montojo, Munich (DE)

(72) Inventor: Francisco Pan-Montojo, Munich (DE)

( * ) Notice: Subject to any disclaimer, the term of this patent is extended or adjusted under 35 U.S.C. 154(b) by 33 days.

(21) Appl. No.: 15/776,817

(22) PCT Filed: Nov. 17, 2016

(86) PCT No.: PCT/EP2016/078061
§ 371 (c)(1),
(2) Date: May 17, 2018

(87) PCT Pub. No.: WO2017/085215
PCT Pub. Date: May 26, 2017

(65) Prior Publication Data
US 2018/0325849 A1    Nov. 15, 2018

(30) Foreign Application Priority Data
Nov. 17, 2015 (EP) ................... 15003289

(51) Int. Cl.
*A61K 31/19* (2006.01)
*A61K 45/06* (2006.01)
*A61P 9/10* (2006.01)

(52) U.S. Cl.
CPC .............. *A61K 31/19* (2013.01); *A61K 45/06* (2013.01); *A61P 9/10* (2018.01)

(58) Field of Classification Search
CPC ............ A61K 31/19; A61K 45/06; A61P 9/10
See application file for complete search history.

(56) References Cited

U.S. PATENT DOCUMENTS 5,516,799 A * 5/1996 Alliger .................... A61K 31/19
                                                           514/557
2011/0021466 A1   1/2011 Villarreal et al.

FOREIGN PATENT DOCUMENTS

WO    0112130 A1    2/2001
WO    2007059631 A1    5/2007

OTHER PUBLICATIONS

Perricone and Dinardo "Photoprotective and Antiinflammatory Effects of Topical Glycolic Acid," Dermatologic Surgery vol. 22, Issue 5 May 1996 pp. 435-437 (Year: 1996).*
Saito et al. "Early increases in TNF-α, IL-6 and IL-β levels following transient cerebral ischemia in gerbil brain.," Neuroscience Letters vol. 206, Issues 2-3, Mar. 15, 1996, pp. 149-152 (Year: 1996).*
Bashir et al. "UVB and pro-inflammatory cytokines synergistically activate TNF-α production in keratinocytes through enhanced gene transcription," J Invest Dermatol. Apr. 2009; 129(4): 994-1001 (Year: 2009).*
Tang et al. "The Cardioprotective Effects of Citric Acid and L-Malic Acid on Myocardial Ischemia/Reperfusion Injury," Evidence-Based Complementary and Alternative Medicine vol. 2013, Article ID 820695, 11 page, Received Dec. 26, 2012; Revised Apr. 3, 2013; Accepted Apr. 4, 2013 (Year: 2013).*
Tang et al. Molecules 2018, 23(4), 863; https://doi.org/10.3390/molecules23040863 Received: Feb. 26, 2018 / Revised: Apr. 8, 2018/Accepted: Apr. 9, 2018/ Published: Apr. 10, 2018 (Year: 2018).*
Toyoda, Y. et al., "Products of the Parkinson's disease-related glyoxalase DJ-1, D-lactate and glycolate, support mitochondrial membrane potential and neuronal survival", Biology Open, 2014, pp. 1-8, © 2014. Published by The Company of Biologists Ltd; DOI: 10.1242/bio.20149399.

* cited by examiner

Primary Examiner — Jeffrey S Lundgren
Assistant Examiner — William Y Lee
(74) Attorney, Agent, or Firm — Blue Filament Law PLLC

(57) ABSTRACT

The present invention relates to glycolic acid or a pharmaceutically acceptable salt or ester thereof for use in the treatment or prevention of ischemic damage. In a preferred embodiment the present invention relates to a method for decreasing cell death caused by an ischemic insult comprising contacting glycolic acid or a pharmaceutically acceptable salt or ester thereof with hypoxic tissue, in particular cortical neurons or myocardial tissue.

10 Claims, 6 Drawing Sheets

Figure 1:
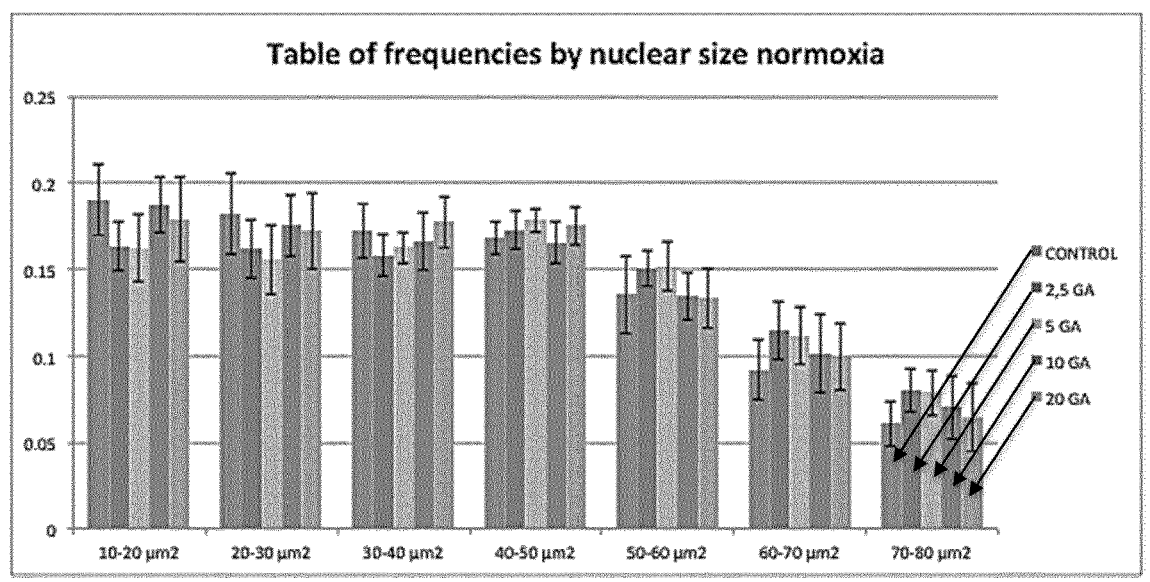

| Mean | 5 mM | CONTROL |
|---|---|---|
| 10-30 µm2 | 0,5796 | 0,690387977 |
| 30-80 µm2 | 0,4204 | 0,309612023 |
| | | |
| Stdv | 5 mM | CONTROL |
| 10-30 µm2 | 0,0689 | 0,150310495 |
| 30-80 µm2 | 0,0689 | 0,150310495 |

TTEST vs CONTROL p=0,029923321

| Mean | 10 mM | CONTROL |
|---|---|---|
| 10-30 µm2 | 0,5345 | 0,690387977 |
| 30-80 µm2 | 0,4655 | 0,309612023 |
| | | |
| Stdv | 10 mM | CONTROL |
| 10-30 µm2 | 0,0737 | 0,150310495 |
| 30-80 µm2 | 0,0737 | 0,150310495 |

TTEST vs CONTROL p=0,003892245

| Mean | 20 mM | CONTROL |
|---|---|---|
| 10-30 µm2 | 0,5348 | 0,690387977 |
| 30-80 µm2 | 0,4652 | 0,309612023 |
| | | |
| Stdv | 20 mM | CONTROL |
| 1-30.000 | 0,1035 | 0,150310495 |
| 30.000-80.000 | 0,1035 | 0,150310495 |

TTEST vs CONTROL p=0,00735751 ns using glycolic acid or a pharmaceutically acceptable salt or ester thereof are an option. Such an application during reperfusion would be particularly advantageous. ii) In the case of chronic ischemic insult, glycolic acid or a pharmaceutically acceptable salt or ester thereof may be used to reduce the damage caused by the ischemic insult.

GLYCOLIC ACID PROTECTS AGAINST ISCHEMIC INSULTS

The present invention relates to glycolic acid or a pharmaceutically acceptable salt or ester thereof for use in the treatment or prevention of ischemic damage. In a preferred embodiment the present invention relates to a method for decreasing cell death caused by an ischemic insult comprising contacting glycolic acid or a pharmaceutically acceptable salt or ester thereof with hypoxic tissue, in particular cortical neurons or myocardial tissue.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

BACKGROUND OF THE INVENTION

According to the world health organization (WHO), heart and cerebral ischemia are the most frequent causes of death or invalidity in the world. They are responsible for around 30% of the total deaths and less than 50% of patients will return to independent living during the following year [1].

During ischemia, blood flow is reduced by occlusion of vessels through a thrombus leading to a hypoxic situation and a functional deficit. For example, in a cerebral ischemic attack, there is an area that receives less then 10 mL/100 gr/min. of blood flow (CBF). This area is necrotic within minutes and cannot be saved. Normally, there is tissue surrounding this area that receives between 20 and 50 mL/100 gr/min. of CBF called the penumbra. Low CBF in the penumbra area can only be tolerated for a finite period before permanent cellular injury [2]. A similar process is applicable to any kind of ischemia, difference being the time elapsed until irreversible damage is observed. The recovery of this area is the main objective of all ischemic insult treatments.

Reperfusion strategies are the most effective therapies in these cases but can also result in harmful consequences. There is growing evidence suggesting that oxidative stress [3] and inflammation [4] are implicated in the pathology of ischemia-reperfusion damage. Moreover, some studies suggest that the latter factor could be regulated by oxidative stress [5] [6]. Up-to-date there are no treatments available capable of reducing the toxicity of reperfusion and reducing the size of the ischemic area.

In humans, environmental factors such as high-fat diets, especially those containing saturated and trans fats and the addiction to certain substances such as tobacco and alcohol increase the risk of suffering a stroke or heart attack. Until now, despite all methods developed to reduce the size of an ischemic insult, there are no substances in the market known to have this kind of positive effect.

The main parameter influencing the functional outcome of an ischemic insult is the size of the death tissue. This is influenced by the time to treatment ("time is tissue"), the age of the patient and the pre-existence of arterial collaterals partially irrigating the area. As discussed, the identification of compounds capable of reducing cellular death and reducing the size of the ischemic area is important, since they can be used to increase the health and well-being of patients having suffered and/or are at risk of ischemic disease.

SUMMARY OF THE INVENTION

In light of the prior art the technical problem underlying the present invention is to provide alternative and/or improved means for the prevention and/or treatment of ischemic disease. A further objective of the invention may therefore be considered the identification of a compound that is useful to treat ischemic insults, in particular by reducing cellular death thereby reducing the size of the ischemic area.

This problem is solved by the features of the independent claims. Preferred embodiments of the present invention are provided by the dependent claims.

The invention therefore relates in a first aspect to glycolic acid or a pharmaceutically acceptable salt or ester thereof for use in the treatment of ischemic insults.

Also described herein is a corresponding method of treatment or prevention of ischemic insults, said method comprising the administration of an therapeutically effective amount of glycolic acid or a pharmaceutically acceptable salt or ester thereof to a subject in need thereof.

In one embodiment, the ischemic insult is associated with lack of blood or oxygen supply to a bodily tissue of a subject. In one embodiment, the ischemic insult is characterised by increased necrosis with apoptosis in the affected hypoxic tissue in comparison to oxygenated tissue.

In the examples described herein the effect of glycolic acid on the survival of mouse cortical neurons 24 hours after undergoing ischemia was tested. The experimental results show that glycolic acid significantly decreases neuronal cell death after administration of glycolic acid in comparison to control non-treated cortical neurons undergoing ischemia. To the best knowledge of the inventor, no study has previously tried testing the effect of glycolic acid on ischemic insults and it could not be foreseen that glycolic acid protects against ischemic insults.

In one embodiment of the invention the ischemic insult to be treated using glycolic acid or a pharmaceutically acceptable salt or ester thereof is cerebral ischemia. In one embodiment of the invention the ischemic insult to be treated using glycolic acid or a pharmaceutically acceptable salt or ester thereof is myocardial ischemia. In one embodiment of the invention the ischemic insult to be treated using glycolic acid or a pharmaceutically acceptable salt or ester thereof is peripheral limb disease (a.k.a. peripheral artery disease). In one embodiment of the invention the ischemic insult to be treated using glycolic acid or a pharmaceutically acceptable salt or ester thereof is intestinal infarction. In one embodiment of the invention the ischemic insult to be treated using glycolic acid or a pharmaceutically acceptable salt or ester thereof is an acute ischemic injury. In one embodiment of the invention the ischemic insult to be treated using glycolic acid or a pharmaceutically acceptable salt or ester thereof is a chronic ischemic injury.

In the examples described herein the effect of glycolic acid on the survival of mouse cortical neurons 24 hours after undergoing ischemia was tested. The results show that glycolic acid protects against different degrees of ischemia both when applied before or after the acute ischemic insult. Most importantly, glycolic acid was able to protect against ischemia when applied during reperfusion. This is particularly advantageous in the clinical practice for two reasons: i) It is impossible to foresee when a brain acute ischemic insult (stroke) or other kind of ischemic insult will occur. Therefore, in such acute situations only post-ischemic treatments are possible. The fact that glycolic acid has a protective effect even when applied after an ischemic attack makes it ideal for its use in the clinical practice. ii) There are no preventive treatments to reduce the size of the stroke or other ischemic insult in patients at risk. Patients with a previous stroke or ischemic insult in the clinical history or with concomitant diseases such as high blood pressure, obesity, sleep apnea, periodontal diseases, inflammation, infections, atherosclerosis or cardiac arrhythmias among other factors have an increased risk of suffering from a stroke [7, 8] or an ischemic insult in any other organ such as the heart [9], the limbs [10] or the intestine [11]. In this patients-at-risk glycolic acid could be used, alone or in combination with other substances such as aspirin, to prevent complications and reduce the size of the ischemic lesion in the brain in the event of an ischemic insult In one embodiment of the invention the glycolic acid or a pharmaceutically acceptable salt or ester thereof is to be applied orally or intravenously. Suitable administration forms for oral or intravenous administration are known to one skilled in the art. In one embodiment of the invention the ischemic insult to be treated using glycolic acid or a pharmaceutically acceptable salt or ester thereof is a human ischemic insult.

Glycolic acid (GA) has the IUPAC name 2-hydroxyethanoic acid and the molecular formula $C_2H_4O_3$. Glycolic acid is used in the prior art, for example, in the textile industry as a dyeing and tanning agent, in food processing as a flavouring agent and as a preservative, and in the pharmaceutical industry as a skin care agent, in particular as a skin peeling agent. Glycolic acid can also be found in sugar beets, sugarcane and various fruits. Traces of glycolic acid are present, for example, in unripe or green grapes. Glycolic acid is also found in pineapple and cantaloupe.

A pharmaceutically acceptable salt of glycolic acid includes but is not limited to potassium gylcolate, sodium gylcolate, calcium gylcolate, magnesium gylcolate, barium glycolate, aluminium gylcolate, oxalate, nitrate, sulphate, phosphate, fumarate, succinate, maleate, besylate, tosylate, tartrate, and palmitate. The production of salts of glycolic acid and the necessary acids used during productions of said salts are within the capabilities of a skilled person.

A pharmaceutically acceptable ester of glycolic acid includes but is not limited to methyl glycolate, ethyl glycolate, butyl glycolate, lauryl glycolate, piperidyl(2)-glycolic acid ethyl, (3-thienyl)-glycolic acid, myristyl glycolate, quinolyl glycolate and cetyl glycolate [12-15]. Ester compounds of GA may be determined and synthesized by a skilled person as is required without undue effort. In some embodiments the ester is intended to enable cleavage of the ester in vivo, thereby releasing GA as the active component.

In a further aspect the invention relates to a composition comprising glycolic acid or a pharmaceutically acceptable salt or ester thereof, and a further ischemia-reducing compound. The term "ischemia-reducing compound" relates to any compound known to exhibit a therapeutic effect with respect to the reduction or prevention of ischemic injury. A number of compounds falling into this category are disclosed herein, by way of example. A skilled person is capable of testing any given compound for their effect on ischemic injury, for example according to the methodology disclosed herein, and requires therefore no undue effort.

In a preferred embodiment the composition comprises an ischemia-reducing compound, wherein the ischemia-reducing compound is an antioxidant. In one embodiment the antioxidant can be one or more of coenzyme Q10, Acetyl-L-Carnitine, R-a-Lipoic acid, selenium and QIAPI-1, in any given combination. In a further embodiment the further ischemia-reducing compound is an inducer of hypometabolism. The inducer of hypometabolism is preferably one or more of ghrelin, the synthetic delta opioid D-Ala(2)-D-Leu (5)-enkephalin, rT3, hibernation trigger, antabolone and bombesin.

In one embodiment of the invention the composition described herein is characterised in that the further ischemia-reducing compound is D-Lactate. In one embodiment of the invention the composition described herein is characterised in that the further ischemia-reducing compound is oxaloacetate. In one embodiment of the invention the composition described herein is characterised in that the further ischemia-reducing compound is a calcium channel blocker. In one embodiment of the invention the composition described herein is characterised in that the the calcium blocker is one or more of MK-801, verapamil, budipine, nifedipine, niquel, 2,3-dihydroxy-6-nitro -7-sulphamoyl-benzo[f]quinoxaline, NP10075, NBQX, PNQX, YM-90K and ZK200775.

D-Lactate has been recently shown to protect against ischemia/reperfusion damage acting as a HCA-I receptor agonist [16]. Oxalacetate has been shown to reduce ischemic damage through the reduction of glutamate toxicity [17]. Inhibition of calcium channels is important because during ischemia/reperfusion there is a toxic calcium overload in the cells that triggers necrosis and apoptosis. There are different types of calcium channels that can be blocked. These include among others voltage-dependent calcium channels, L-type calcium channels, N-type calcium channels, storage operated calcium channels or ligand-dependent calcium channels such as the NMDA-receptor or the AMPA receptors. It has been shown that blocking glutamate dependent calcium channels such as the NMDA-receptor is neuroprotective during stroke. Different calcium channel blockers have been shown to have this effect by reducing the calcium influx induced by glutamate excitotoxicity occurring during ischemia or subarachnoid hemorrage [18, 19]. We expect that the combination of glycolic acid with one or more of these substances has the potential to further reduce ischemic damage through a synergetic mechanism of action.

As used herein, "treating" or the "treatment" of a subject afflicted with a disorder, such as an ischemic disease, shall mean slowing, stopping or reversing the disorder's progression, or the symptoms or consequences of the disorder. In a preferred embodiment, treating a subject afflicted with a disorder means reversing the disorder's progression, ideally to the point of eliminating the disorder itself. As used herein, ameliorating a disorder and treating a disorder are equivalent.

The treatment of the present invention may also, or alternatively, relate to a prophylactic administration of the therapeutic component of the present invention, namely glycolic acid or a pharmaceutically acceptable salt or ester thereof. Such a prophylactic administration may relate to the prevention of any given medical disorder, such as the prevention of ischemic insult, or the prevention of development of said disorder, whereby prevention or prophylaxis is not to be construed narrowly under all conditions as absolute prevention. Prevention or prophylaxis may also relate to a reduction of the risk of a subject developing any given medical condition, preferably in a subject at risk of said condition.

The treatment described in the present invention, comprising the administration of glycolic acid or a pharmaceutically acceptable salt or ester thereof, is intended that the glycolic acid or a pharmaceutically acceptable salt or ester thereof is one of the active agents administered to a subject.

Glycolic acid may, for example, be present as a structural component in nanoparticles or other biocompatible scaffolds in order to deliver other therapeutic substances. In one embodiment of the present invention the treatment described herein therefore does not comprise administration of nanoparticles, biocompatible scaffolds, or other potentially similar structural components in which glycolic acid is present. In such cases, the glycolic acid is present merely as a structural component and not as an active agent. The present invention is related to the administration of glycolic acid or a pharmaceutically acceptable salt or ester thereof as an active agent, preferably in a form that enables free, unbound and/or soluble glycolic acid to be uptaken by the subject of treatment.

The terms "ischemic insult", "ischemic disease" or "ischemic disorder" are used interchangeably herein, and designate the acute or sub-acute interruption of the blood supply to one or more bodily tissues. As discussed herein, ischemic insults are commonly due to the occlusion of an artery, either by: i) arteriosclerosis, ii) the rupture of an arteriosclerotic plaque or an aneurisma with or without the in situ formation of a clot, iii) the rupture of an artery causing an haemorrhage or iv) an embolic event in which a clot (arterio-arterial or veno-arterial embolism), an air bubble (gaseous embolism) or lipid tissue (lipid embolism) formed elsewhere is transported in the blood until it occludes an artery with a smaller diameter.

In one embodiment the invention relates to the treatment of brain global ischemia. Brain global ischemia is a particular condition in which there is insufficient blood flow to the brain to meet metabolic demand. This leads to poor oxygen supply or cerebral hypoxia and thus to the death of brain tissue or cerebral infarction/ischemic stroke. This general reduction of blood supply to the brain is normally due to a heart failure or a dramatic drop in the blood pressure. The main parameters influencing the functional outcome of an ischemic event are the cellular death rate and the size of ischemic tissue, both aspects of the disease being interrelated with one another.

In particular embodiments of the invention ischemic disease to be treated and/or prevented may be (a) cerebral ischemia, in particular stroke and subarachnoid hemorrhage, vascular dementia and/or infarct dementia; (b) myocardial ischemia, in particular a coronary heart disease and/or myocardial infarction; (c) peripheral limb disease, in particular periphery arterial occlusive disease, (d) renal and/or intestinal ischemia, in particular intestinal infarction due to the occlusion of the celiac or mesenteric arteries.

With respect to the prevention of ischemic disease in a patient at risk thereof, the patient at thereof may demonstrate one or more of the following indications: (a) shows symptoms or indications of being at risk of developing a ischemic disease, such as high blood cholesterol and triglyceride levels, high blood pressure (wherein references to "high" levels refer to levels above the average population values), the presence of diabetes and prediabetes, overweight, tobacco smoking, lack of physical activity, an unhealthy diet and/or stress; (b) shows any risk markers in ex vivo tests, in particular in blood samples; (c) has previously suffered from an ischemic disease, in particular had a cerebral or myocardial ischemia; and/or (d) has a predisposition of developing a cardiovascular ischemic disease, in particular a genetic predisposition.

The term "patient at risk" may refer to any subject who is at risk of developing a disease condition in the sense of the present invention, in particular with respect to those indications of risk described above under (a) to (d). Preferably, the risk of developing a disease condition for this subject is at least 5%, at least 10%, at least 25%, at least 50%, at least 75%, at least 100%, at least 150%, at least 200%, at least 300%, at least 500%, or more than 500% higher compared to the average risk throughout the population. The patient in the sense of the present invention may be any subject who can develop a cardiovascular ischemic disease or condition in the sense of the present invention. Preferably, the patient is a mammal, in particular a human.

Ischemic diseases include circulatory disorders, cardiovascular disease, artery or blood vessel conditions and/or ischemic obstructive or occlusive diseases or conditions, or other states of vascular tissue where blood flow is, or can become, impaired or altered from normal levels. Examples of vascular conditions or vascular diseases to which the methods of the invention apply are those in which the vasculature of the affected tissue or system is senescent or otherwise altered in some way such that blood flow to the tissue or system is reduced or in danger of being reduced or increased above normal levels. It refers to any disorder in any of the various parts of the cardiovascular system, which consists of the heart and all of the blood vessels found throughout the body.

Diseases of the heart may include coronary artery disease, cardiomyopathy, valvular heart disease, pericardial disease, congenital heart disease (e.g., coarctation, atrial or ventricular septal defects), and heart failure. Diseases of the blood vessels may include arteriosclerosis, atherosclerosis, hypertension, stroke, vascular dementia, aneurysm, peripheral arterial disease, intermittent claudication, vasculitis, venous incompetence, venous thrombosis, varicose veins, and lymphedema. Circulatory disorders may relate to various organs such as brain, heart, kidney, adrenal and lung. Peripheral arterial occlusive disease (PAOD; also referred to as peripheral arterial disease (PAD)) may result from atherosclerotic or inflammatory processes producing arterial stenosis, or from thrombus formation associated with underlying atherosclerotic disease. A common site for PAOD is in the lower limbs. This process of atherosclerosis causes initial thickening and plaque formation encroaching the arterial lumen, decreasing the effective luminal radius of afflicted arterial segments, producing an anatomic and sometimes functional obstruction to blood flow.

The term "neuron" as used herein is a mature specialized cell that transmits and processes information within the nervous system, both peripheral and central. In mammals, neurons are formed during development and do not have the ability to divide and regenerate the nervous tissue upon damage. Treating or preventing an unwanted ischemic detrimental effect on neurons via administration of GA or a pharmaceutically acceptable salt or ester thereof is one object of the invention.

Other cell types that are incapable of effective regeneration are also targets of the therapeutic effect of the present invention. For example, cardiomyocytes also exhibit a limited regeneration capacity and may be damaged by ischemia. Treating or preventing an unwanted ischemic detrimental effect on cardiomyocytes via administration of GA or a pharmaceutically acceptable salt or ester thereof is one object of the invention.

In one embodiment the invention is directed towards the treatment of acute ischemic injury. The term "acute ischemic injury" as used herein is directed to physiological processes or medical conditions, such as those described herein, that develop in a relatively short time frame, for example within 24 hours from onset, more preferably within 12 hours from onset. An ischemic injury can leave long-lasting or permanent damage to the brain after a very short time, for example irreversible damage, for example necrosis, can occur within one hour, but may occur within shorter time frames, such as after a few minutes, for example after 5 minutes, 10 minutes or 30 minutes, after onset of ischemia. The treatment of acute ischemic injury is, in one embodiment, directed to a treatment of the injury as soon as possible after development of a disease state, such as within 24 hours, 12 hours, or 1 hour of the onset of the ischemia. Each tissue has a difference resistance to ischemia, depending on the cell type and the amount of collateral irrigation, but even the most resistant tissues start to develop necrosis within the first few hours (intestinal tissue is one of the most resistant but within 10 hours symptoms and necrosis of the tissue is expected).

In one embodiment the invention is directed towards the treatment of chronic ischemic injury. The term "chronic ischemic injury" relates to physiological processes or medical conditions that persist beyond 24 hour after onset, and may persist for multiple days, weeks, months or years after onset. An example of chronic ischemic injury is vascular dementia.

In accordance with the present invention the glycolic acid or a pharmaceutically acceptable salt or ester thereof may be comprised in a formulation or pharmaceutical composition. A formulation prepared in accordance with the invention comprises at least two components in an appropriate relationship two each other, wherein at least one of the two components is glycolic acid or a pharmaceutically acceptable salt or ester thereof. The second of the at least two components of a formula may be a simple carrier, for example water. A formulation may be a mixture or a structure such as a liquid, a capsule, a powder, an aerosol, a pill, a tablet, or an emulsion, prepared according to a specific procedure (called a "formula"). Formulations are a very important aspect of creating drugs. Formulas may ensure, for example, that the active ingredient of a drug—being in the present invention glycolic acid or a pharmaceutically acceptable salt or ester thereof—is delivered to the correct part of the body, in the right concentration, and/or at the right release rate (not too fast and not too slowly).

The formulation of the present invention is therefore preferably a pharmaceutical formulation. In accordance with the present invention, the term "pharmaceutical formulation" or "pharmaceutical composition" relates to a formulation for administration to a mammal, preferably a human. The pharmaceutical formulation of the invention may, optionally, comprise further molecules, for example compounds being capable of altering the characteristics of the compounds of the invention thereby, for example, stabilizing, modulating and/or activating their function. The pharmaceutical formulation of the present invention may, optionally and additionally, comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, organic solvents including DMSO etc. Formulations comprising such carriers can be formulated by well-known conventional methods. These pharmaceutical formulations can be administered to the subject at a suitable dose. The dosage regimen will be determined by the attending physician and clinical factors. As is well known in the medical arts, dosages for any one mammal depend upon many factors, including the mammal's size, body surface area, age, the particular compound to be administered, sex, time and route of administration, general health, and other drugs being administered concurrently. The therapeutically effective amount for a given situation will readily be determined by routine experimentation and is within the skills and judgement of the ordinary clinician or physician.

The glycolic acid or a pharmaceutically acceptable salt or ester thereof according to the present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, subcutaneously, subconjunctival, intravesicularly, mucosally, intrapericardially, intraumbilically, intraocularly, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The instant disclosure also includes kits, packages and multi-container units containing the herein described pharmaceutical formulations, active ingredients, and/or means for administering the same for use in the prevention and treatment of diseases and other conditions in mammalian subjects.

Glycolic acid (GA) is naturally present in a variety of fruits, vegetables, meats and beverages, however in amount being lower as 50 mg/kg (see Harris and Richardson (1980), Investigative Urology, 18:106-109). 50 mg/kg correspond to 0.005% (w/w). Hence, the formulation of the invention preferably comprises a higher amount/concentration of glycolic acid or a corresponding pharmaceutically acceptable salt or ester thereof than the amount of glycolic acid found in natural food.

The skilled person can determine a suitable dose of such formulations as well as a suitable dosage in case glycolic acid or a pharmaceutically acceptable salt or ester thereof are directly administered to a subject. The administered amounts of glycolic acid or a pharmaceutically acceptable salt or ester thereof on the one hand have to be sufficient for the treatment or prevention of ischemic injuries, and on the other hand should not be so high as to generate an acidosis in the subject to be treated. Acidosis is an increased acidity in the blood and other body tissue. Acidosis is said to occur when the blood, serum or body tissue pH falls below 7.35. Means and methods to determine the pH in blood, serum and body tissue are well-known. Suitable does will be discussed herein below.

The toxic effect of too much glycolic acid is known, for example, from the 1985 diethylene glycol wine scandal. The scandal involved a limited number of Austrian wineries that had illegally adulterated their wines using the toxic substance diethylene glycol (a primary ingredient in some brands of antifreeze) to make the wines appear sweeter and more full-bodied. The major cause of toxicity is not the ethylene glycol itself but its major metabolite glycolic acid. The minimum toxic dose of diethylene glycol is estimated at 0.14 mg glycolic acid per kg of body weight and the lethal dose is estimated between 1.0 and 1.63 g/kg. Hence, the preferred dose of glycolic acid and a pharmaceutically acceptable salt or ester thereof is selected such that total glycolate levels do not exceed 0.20 mg glycolate per kg of body weight, preferably do not exceed 0.14 mg glycolate per kg of body weight, and more preferably do not exceed 0.10 mg. Preferred lower amounts to be combined with the maximum amount are with increasing preference 0.01, 0.03, 0.05, 0.075 and 0.1 mg glycolate per kg of body weight.

The therapeutic route used for the treatment or prevention of ischemic damage is not limited. Hence, administration may be topical (local), enteral (system-wide effect, but delivered through the gastrointestinal tract), or parenteral (systemic action, but delivered by routes other than the GI tract). As regards system-wide applications the oral or intravenous route are preferred.

It is though preferred that the glycolic acid or a pharmaceutically acceptable salt or ester thereof is applied directly where its action is desired and hence is intravenously, more preferably such that it is directly contacted with the occluded artery that caused the ischemia region after recanalization to allow the quick administration of glycolic acid to the affected area and prevent ischemia-reperfusion damage. It is to be understood that the above discussed glycolate amounts per kg of body weight has to be taken into account in particular if glycolic acid or a pharmaceutically acceptable salt or ester thereof are enterally or parenterally administered. Preferred concentrations and amounts of glycolic acid or a pharmaceutically acceptable salt or ester thereof to be present locally in the blood irrigating the ischemic area will be further discussed herein below. Also means for directly contacting glycolic acid or a pharmaceutically acceptable salt or ester thereof with the ischemic region are provided herein below.

In accordance with a preferred embodiment of the invention, ischemic insults are associated with the appearance of necrosis and apoptosis in the tissue.

Necrosis and apoptosis are the medical terms to describe cell death. Necrosis and apoptosis are two forms of cell death. In necrosis cells die suddenly releasing the cellular content to the extracellular matrix and inducing an inflammatory reaction. Apoptosis is a sub-acute process that occurs after an insult or aggression that results in the activation of an automatic cell death program.

The ischemic diseases and insults described herein are typically characterised by the common feature of increased necrosis and apoptosis in the tissue exhibiting reduced blood flow and a corresponding hypoxia. In light of the examples provided herein, the written disclosure of the invention and the capabilities of a skilled person, the treatment of ischemic disease as such is sufficiently supported due to the technical effect of glycolic acid or a pharmaceutically acceptable salt or ester thereof on fundamental pathological components (reducing cellular death and reducing the size of the ischemic area) that are evident in a broad range of ischemic diseases, for example those disclosed herein.

The two aspects analysed in order to diagnose the severity of neuronal cell death after ischemia are: the percentage of apoptotic nuclei (characterized by a decrease in the nuclear size when compared to normoxic conditions), and a count of the total number of neurons alive after 24 hours.

In accordance with a further preferred embodiment of the invention, the glycolic acid or a pharmaceutically acceptable salt or ester thereof is to be applied inside the occluded artery during the mechanical recanalization or systemically together with or after systemic fibrinolysis. In the case of global brain ischemia, glycolic acid can also be applied alone during the treatment to restore a normal cardiovascular function in order to protect the neuronal tissue.

In order to treat or prevent the consequences of an ischemic insult by reducing the size of the ischemic area the glycolic acid or a pharmaceutically acceptable salt or ester thereof is preferably directly contacted with the cortical neurons during recanalization. This may be done by applying glycolic acid or a pharmaceutically acceptable salt or ester thereof to the patient in accordance with the above-preferred embodiment of the invention. In accordance with the above preferred embodiment the glycolic acid or a pharmaceutically acceptable salt or ester thereof is preferably comprised in the composition of the solvent carrying the fibrinolitic compound (tissue plasminogen activator (tPA, also known as IV rtPA, given through an IV in the arm) or applied through the intra arterial catheter after mechanical recanalization.

In accordance with another preferred embodiment of the invention, the ischemic insult is human ischemic insults.

In accordance with still another preferred embodiment of the invention, the ischemic insult is ischemia in a mammalian domestic animal, zoo mammal or endangered mammal.

In addition to ischemic insult in humans also the treatment of ischemic insults in mammalian production animals or mammalian domestic animal is of great commercial interest. Non-limiting examples of production animals or mammalian domestic animal are cat, dog, cattle, horse, donkey, mouse, rat, rabbit, pig, sheep, goat and Guinea pig. Non-limiting examples of a zoo mammal or a endangered mammal are elephants, tigers, leopard, lion, ape (e.g. gorilla or chimpanzee), monkey (e.g. lion tamarin), giraffe, rhino, polar bear, buffalo, dolphin and whale.

In accordance with a preferred embodiment of the method of the invention, the further compound is/are (i) an antioxidants, preferably coenzyme Q10, Acetyl-L-Carnitine, R-α-Lipoic acid, selenium and QIAPI-1, (ii) substances inducing hypometabolism, preferably ghrelin, the synthetic delta opioid D-Ala(2)-D-Leu(5)-enkephalin, rT3, hibernation trigger, antabolone, bombesin.

In accordance with a preferred embodiment of the invention, the glycolic acid or a pharmaceutically acceptable salt or ester thereof is used/comprised at least at a concentration of 1 mM, 2.5 mM, preferably 5 mM, more preferably 10 mM and most preferably 20 mM. Concentrations of up to 40 mM, or in some cases up to 60 mM, are encompassed by some embodiments of the present invention.

In accordance with this preferred embodiment and preferred examples thereof the indicated concentration of glycolic acid or a pharmaceutically acceptable salt or ester thereof designates the final concentration of glycolic acid or a pharmaceutically acceptable salt or ester thereof in the ischemic tissue to be used/treated.

For the intraarterial injection of the compound during recanalization, this concentration can, in one embodiment, be determined by calculating the volume of tissue affected by the artery either by looking at CT and/or MRT images, or by estimating the volume irrigated by the occluded part of the artery based on previously gained anatomy knowledge and experimental data. Once the volume is determined, the volume of glycolic acid with a given concentration to be administered can be calculated to achieve the final required concentration.

If glycolic acid is to be administered systemically, the amount administered will be determined based on the body surface area, a parameter based on a combination of body weight and height. The following five methods to calculate the body surface area (BSA) are all equally valid for our purpose:

Mosteller (Mosteller R D. Simplified Calculation of Body Surface Area. N Engl J Med. 1987 Oct. 22; 317(17):1098): BSA (m$^2$)=√(height (cm)×weight (kg)/3600).

DuBois & DuBois (DuBois D, DuBois E F. A formula to estimate the approximate surface area if height and weight be known. Arch Int Med 1916 17:863-71): BSA (m$^2$)= 0.20247×height (m)$^{0.725}$×weight (kg)$^{0.425}$.

Haycock (Haycock G B, Schwartz G J, Wisotsky D H. Geometric method for measuring body surface area: A height weight formula validated in infants, children and adults. The Journal of Pediatrics 1978 (93):1:62-66): BSA (m$^2$)=0.024265× height (cm)$^{03964}$×weight (kg)$^{0.5378}$.

Gehan & George (Gehan E A, George S L. Estimation of human body surface area from height and weight. Cancer Chemother Rep 1970 54:225-35): BSA (m$^2$)=0.0235×height (cm)$^{0.42246}$×weight (kg)$^{0.51456}$.

Boyd (The growth of the surface area of the human body. Minneapolis: University of Minnesota Press, 1935): BSA (m$^2$)=0.0003207×height (cm)0.3× weight (grams)$^{0.7285-}$ (0.0188×log(weight).

As it is evident from the examples and figures herein below the concentration of glycolic acid used for the experiments with mouse cortical neurons was 2.5 and 5 mM before ischemia and 10 and 20 mM during reperfusion. Moreover, as glycolic acid at 10 mM increased cortical neurons survival and decrease the ischemic area in mouse cortical neurons it can be assumed that this concentration or higher also increases neuronal survival and reduces ischemic area in other mammalian species, in particular humans. Also lower concentrations of glycolic acid or a pharmaceutically acceptable salt or ester thereof of at least 2.5 mM or of at least 5 mM are believed to reduce the ischemic area by increasing the cell survival rate. In one embodiment the cell survival rate is calculated as the number of cells alive (measured as the cells with an intact nuclei of normal size (>30 μm$^2$)) divided by the total number of cells (including cells with normal size nuclei and apoptotic or necrotic cells with picnotic nuclei (<30 μm$^2$).

With respect to the above preferred embodiments of the invention it is preferred that the glycolic acid or a pharmaceutically acceptable salt or ester thereof is used/comprised at the most at a concentration of between 1 mM to 40 mM, such as 20 mM, preferably 10 mM, more preferably 5 mM. As regards preferred ranges, the various indicated individual minimum and maximum concentration may be freely combined. Hence, contemplated are by the present invention, inter alia and with increasing preference concentration ranges of 2.5 mM to 30 mM and 5 mM to 20 mM.

The glycolic acid or a pharmaceutically acceptable salt or ester thereof may be administered or used at least in amounts of about 10 μg/2 endangered cortical neurons to 5000 μg/2 million cortical neurons, preferably 100 μg/2 million cortical neurons to 2000 μg/2 million cortical neurons, more preferably about 190, 125 μg/2 million cortical neurons, or about 380.25 μg/2 million cortical neurons, or about 760.5 μg/2 million cortical neurons, and most preferably about 1521 μg/2 million cortical neurons.

In accordance with this preferred embodiment the indicated concentration of glycolic acid or a pharmaceutically acceptable salt or ester thereof designates the amount of glycolic acid or a pharmaceutically acceptable salt or ester thereof in the tissue to be used/treated based on the mean value of 2 million neurons per ml tissue volume. The indicated amounts of glycolic acid or a pharmaceutically acceptable salt or ester thereof are particularly useful in case the ischemic insult is an ischemic insult that occurred within the last hour. Based on the exemplified amounts of glycolic acid or a pharmaceutically acceptable salt or ester thereof for cortical neurons the skilled person can calculate the amounts of glycolic acid or a pharmaceutically acceptable salt or ester for other mammals based on the mean value of neurons/ml of tissue volume in the respective mammal.

In one embodiment the invention also relates to an ex vivo method for increasing the survival of cortical neurons and reducing the size and/or severity of ischemic insult, comprising contacting glycolic acid or a pharmaceutically acceptable salt or ester thereof with the cortical neurons. In one embodiment the cortical neurons are mouse primary cortical neurons.

FIGURES

The following figures are presented in order to describe particular embodiments of the invention, by demonstrating a practical implementation of the invention, without being limiting to the scope of the invention or the concepts described herein. The figures show:

FIG. 1: Table of frequencies by nuclear size during normoxia in cortical primary neuronal cultures in vivo.

Figure 2:
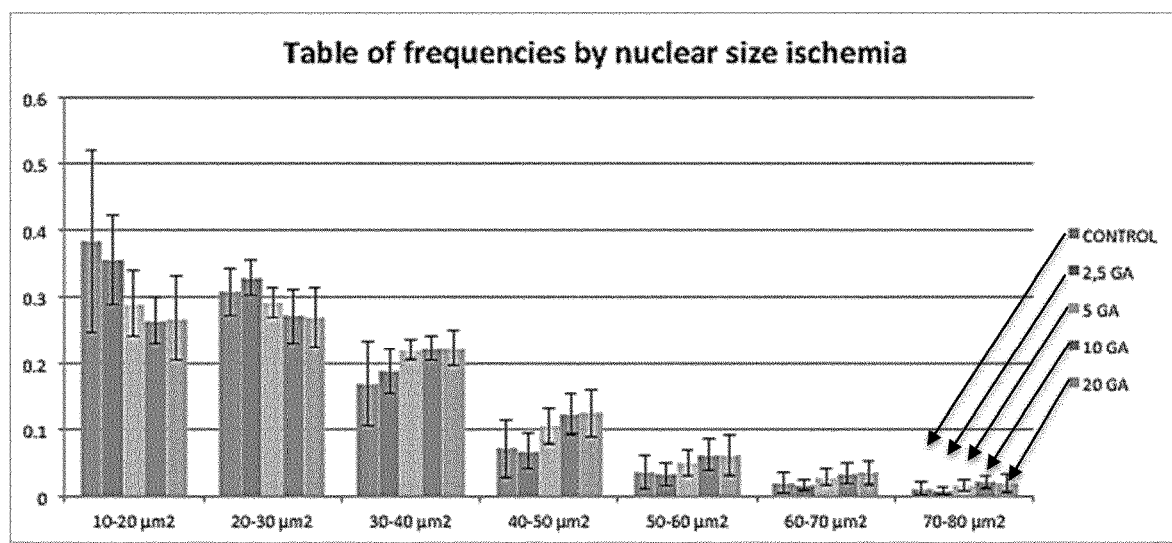

FIG. 2: Table of frequencies by nuclear size after ischemia on cortical primary neuronal cultures. Ischemia induces a shift of the nuclear size increasing the number of smaller apoptotic nuclei. This shift is partially reversed by the pretreatment with 2.5 mM and 5 mM glycolic acid or with the treatment during reperfusion with 10 and 20 mM glycolic acid.

Figure 3:
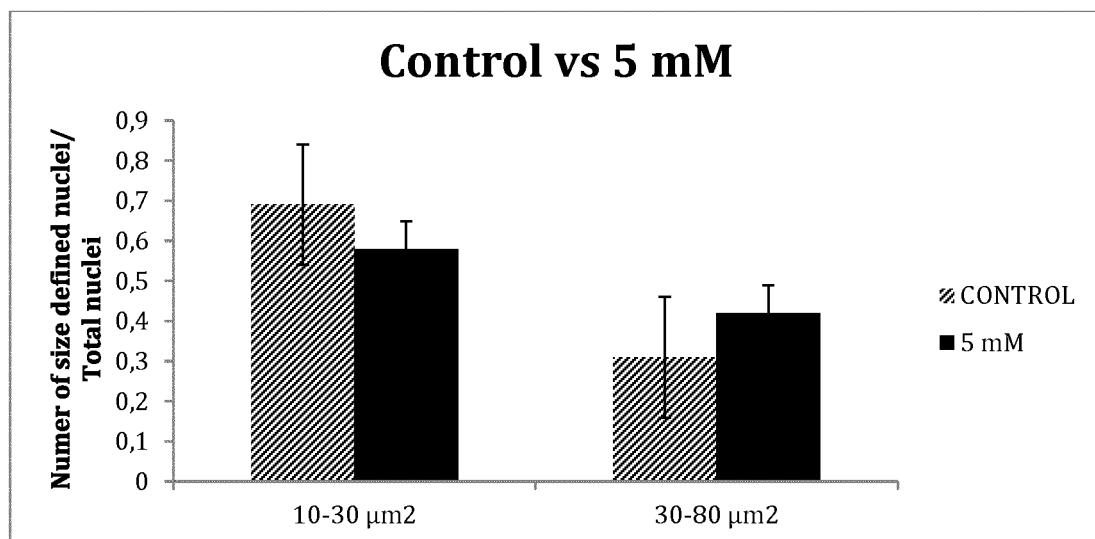

FIG. 3: Pre-treatment with 5 mM of glycolic acid reduces the number of apoptotic neurons (nuclear size <30 mM) during ischemia. Effect of the pre-treatment with 5 mM glycolic acid on the nuclear size of cortical neurons as compared to non-treated neurons during ischemia. p<0.05.

Figure 4:
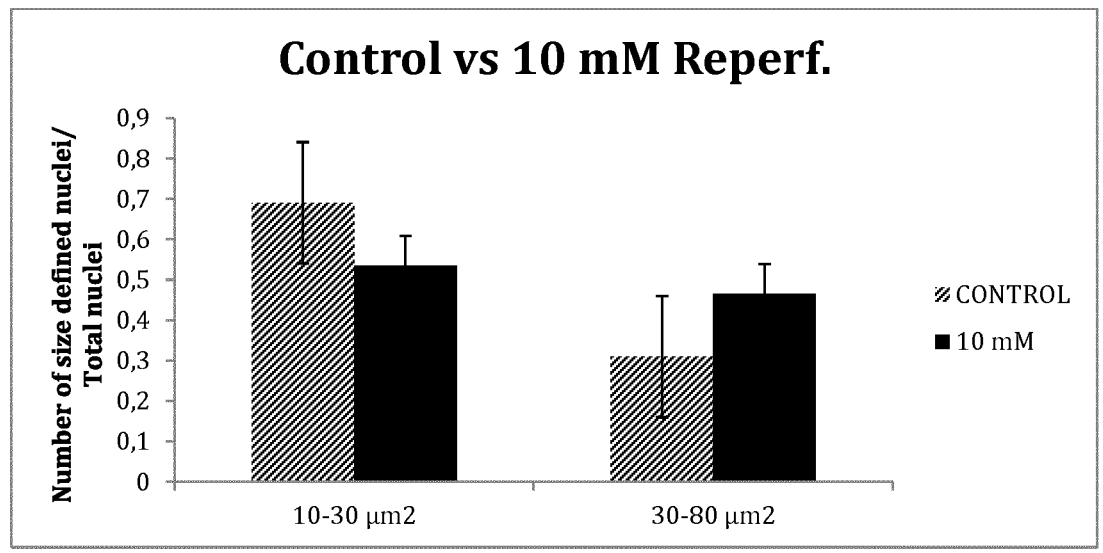

FIG. 4: Treatment with 10 mM of glycolic acid during reperfusion reduces the number of apoptotic neurons (nuclear size <30 mM) after ischemia. Effect of the treatment with 10 mM glycolic acid during reperfusion on the nuclear size of cortical neurons as compared to non-treated neurons during ischemia. p<0.01

Figure 5:
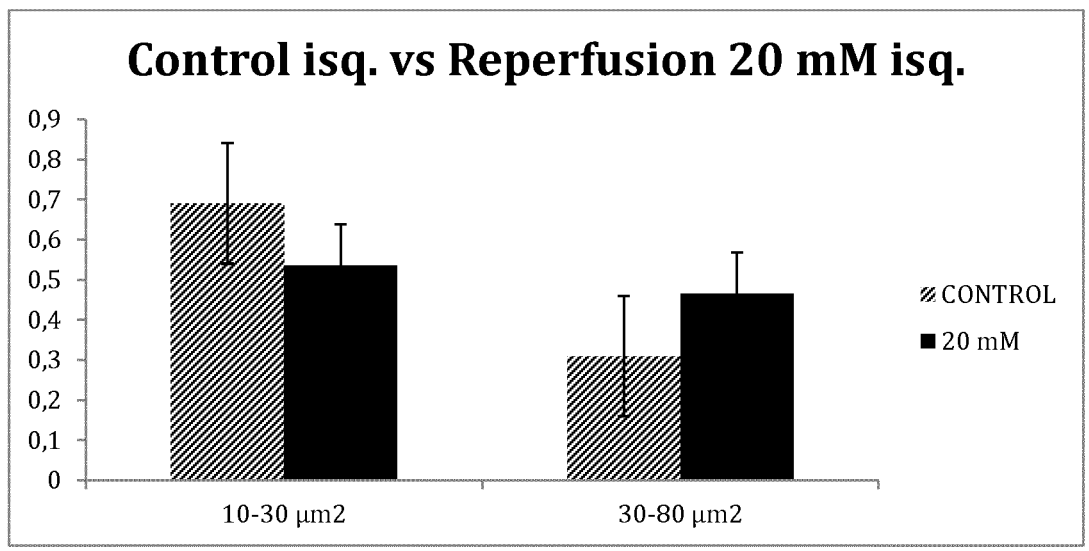

FIG. 5: Treatment with 20 mM glycolic acid during reperfusion reduces the number of apoptotic neurons (nuclear size<30 mM) after ischemia. Effect of the treatment with 20 mM glycolic acid during reperfusion on the nuclear size of cortical neurons as compared to non-treated neurons during ischemia. p<0.01

Figure 6:
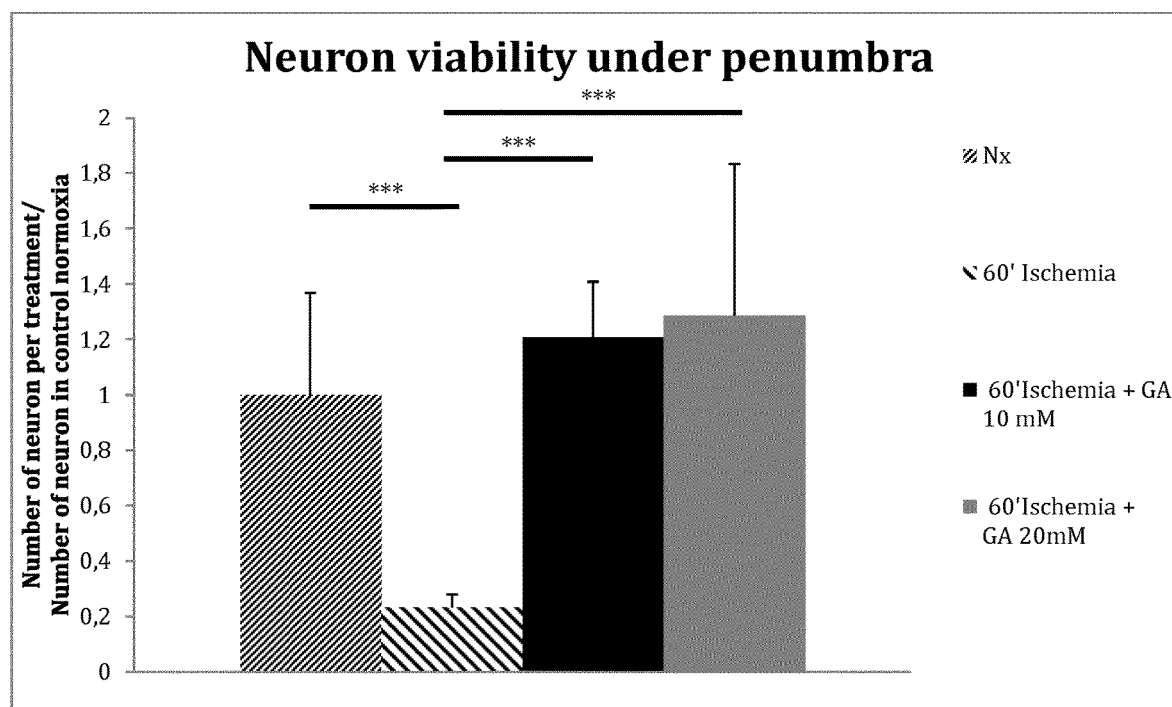

FIG. 6: Treatment with 10 mM or 20 mM glycolic acid during reperfusion increases the survival rate of mouse cortical neurons measured 24 hours after a 60 minutes-long ischemic insult. P<0.001.

Figure 7:
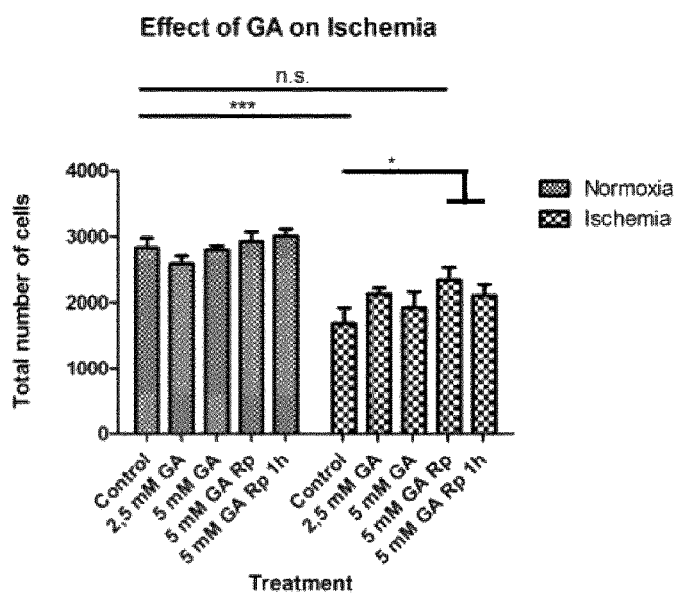

FIG. 7: Treatment with 2.5 mM or 5 mM glycolic acid during reperfusion increases the survival rate of mouse cortical neurons measured 24 hours after a 45 minutes ischemic insult. Error bars show s.e.m. * means P<0.05

Figure 8:
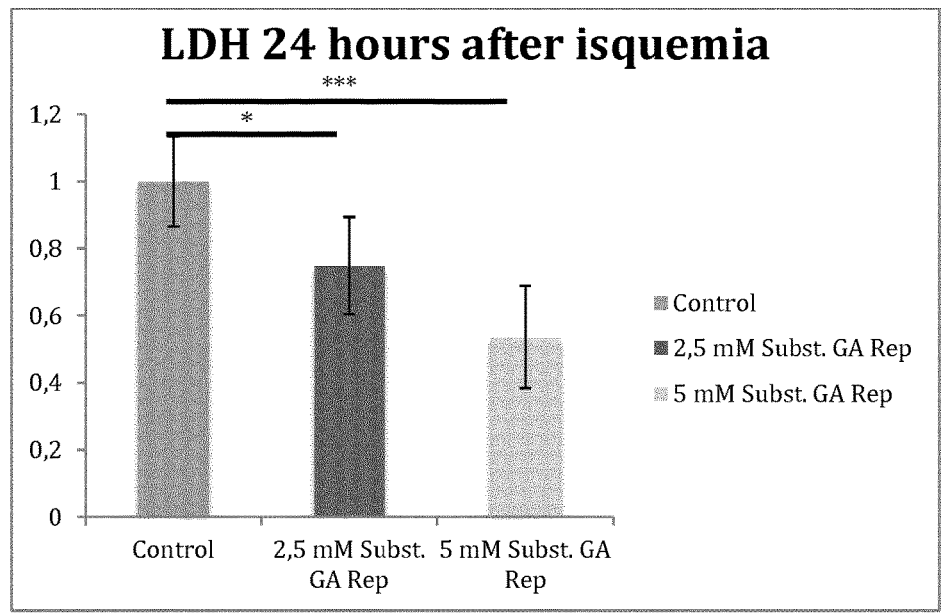

FIG. 8: Treatment with 2.5 and 5 mM glycolic acid (2,5 and 5 mM rep. GA) during reperfusion after ischemia reduces apoptosis (shown as a reduction in the concentration of LDH after 24 hours when compared to ischemic non-treated neurons) in mouse cortical neurons measured 24 hours after a 45 minutes ischemic insult. * means p<0.05, *** means p<0.001. Error bars shown standard deviation.

Figure 9:
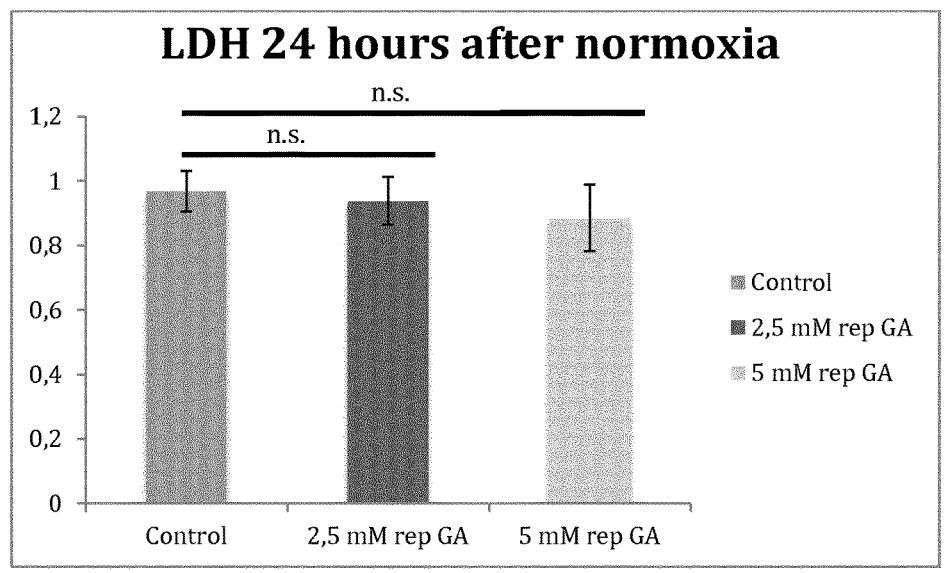

FIG. 9: Graphic showing the effect of glycolic acid after normoxia. The effect of glycolic acid on maintaining LDH levels reduced during ischemia is specific, as it cannot be observed during in normoxic conditions. n.s. means not significant.

EXAMPLES

The invention is further described by the following examples. These are not intended to limit the scope of the invention.

Example 1

Material and Methods

Models of Stroke:

In Vitro Model of Stroke:

In order to mimic neuronal ischemia in vitro, primary cortical neurons were culture in vitro for 6 days. After this time either a total ischemia or a partial ischemia were performed.

Total ischemia: on the day of ischemia medium was changed to PBS (pH=6.5) that had been previously bubbled with N2 to remove all O2. In the case of total ischemia, in order to ensure total lack of oxygen in the PBS, dithionite was added to the PBS to capture the remaining diluted O2. This process ensured the absence of both nutrients and O2 as it would be expected at the core of a stroke.

Penumbra: to mimic penumbra, normal medium was changed to a mixture of medium without antioxidants and PBS (50:50) and bubbled with N2 to remove diluted O2.

In both protocols neurons were then placed inside a gas chamber filled with N2 and left there for 45 minutes (ischemia) or 1 hour (penumbra). In order to mimic reperfusion, PBS or medium/PBS were then substituted with medium without antioxidants and left in the incubator overnight.

Normoxia: to mimic normoxia, normal medium was changed with normal medium without antioxidants and placed in the incubator under normal conditions for 45 minutes or 1 hour. Then medium was exchanged again with normal medium and left overnight in the incubator.

In all conditions neurons were fixed and stained with DRAQS (a nuclear marker) and NeuN (a neuronal marker) on the next day. Images were taking with an OPERA microscope and analysed with the help of FIJI Image analysis software. The more reliable outcome parameter to detect apoptosis was the surface of the nuclei in $\mu m^2$ and the number of neurons alive after 24 hours. As it can be observed in FIGS. 1 and 2, the frequency distribution of nuclear sizes dramatically changed between normoxia and ischemia without treatment.

Additionally, the amount of LDH released to the media was determined. LDH is released to the media during necrosis (immediate cell death after an insult, 0-6 hours after insult) and in the late stages of apoptosis in vitro (6 to 24 hours after insult) through the disruption of the plasmatic membrane [20]. For this we used the PIERCE LDH CYTOTOXICITY ASSAY from Life Technologies.

In vivo model of stroke:

Transient filament MCA occlusion model (fMCAo): Mice are anaesthetized with isoflurane delivered in a mixture of 30% $O_2$ and 70% $N_2O$. An incision is made between the ear and the eye in order to expose the temporal bone. A laser Doppler probe is affixed to the skull above the MCA territory, and mice are placed in the supine position. An incision is made in the midline neck region, and the common carotid artery and left external carotid artery are isolated and ligated; a 2-mm silicon-coated filament (Doccol, #701912PKRe) is inserted into the internal carotid artery, and MCA occlusion is confirmed by a corresponding decrease in blood flow (i.e., a decrease in the laser Doppler flow signal). After 60 minutes of occlusion the filament is removed and either the vehicle, or 5, 10, 20 or 40 mM of GA (concentration for the total expected infact area) is injected. For the survival period, the mice are kept in their home cage with facilitated access to water and food. Sham-operated mice receive the same surgical procedure, except no filament is inserted. Body temperature is maintained throughout surgery using a feedback-controlled heating pad. GA treated subjects are expected to exhibit less severe decrease in blood flow.

Infarct volumetry: Brains are removed 24 and 72 hours after stroke induction and frozen on powdered dry ice. Coronal cryosections (20-μm thick) are cut at 400-μm intervals. The sections are stained with cresyl violet in accordance with standard protocols and scanned at 600 dpi. Infarct area is measured in each section using ImageJ software (NIH). In the fMCAo model, an edema correction for infarct volume is calculated using the following formula: (Ischemic area)=(Direct lesion volume)−[(Ipsilateral hemisphere)−(Contralateral hemisphere)] was performed. The total infarct volume is calculated by integrating the measured areas and intervals between the sections. Treatment with GA is expected to reduce the infarct volume size.

Models of Myocardial Infarction:

In vivo model of myocardial infarction:

Ischaemia-reperfusion in perfused hearts: Ischemia reperfusion in perfused hearts is performed. After sodium pentobarbital overdose (150 mg/kg i. p.), mouse hearts are quickly excised and perfused through the aorta in a Langendorff apparatus with a modified Krebs-Henseleit bicarbonate buffer (in mmol/l: 140 NaCl, 24 NaHCO3, 2.7 KCl, 0.4 KH2PO4, 1 MgSO4, 1.8 CaCl2 and 11 glucose, 95% O2-5% CO2 at 37° C.) at constant flow perfusion pressure of 80 mmHg. Left ventricular (LV) pressure is monitored with a water-filled latex balloon inserted into the LV and inflated to obtain an end-diastolic pressure (LVEDP) of 6-8 mmHg. LV developed pressure (LVdevP) is calculated as the difference between LV systolic pressure and LVEDP. After 30 minutes (min) of normoxic perfusion, mouse hearts are subjected to 60 min of normothermic global ischaemia followed by 60 min of reperfusion with vehicle or 5, 10, 20 or 40 mM glycolic acid. Lactate dehydrogenase (LDH) activity is spectrophotometrically measured in samples collected from the coronary effluent at different times throughout the perfusion period and was considered an indirect measure of necrosis. After 60 min of reperfusion, heart slices were incubated in 1 triphenyltetrazolium chloride to outline the area of necrosis. Hearts submitted to normoxic perfusion during 120 min served as time control series. Areas of necrosis between normoxic, ischemic vehicle-treated and ischemic glycolic acid-treated are compared. Treatment with GA is expected to lead to reduced necrosis compared to controls.

In Vitro Model of Myocardial Infarction:

Ischaemia-reperfusion in isolated cardiomyocytes: Freshly isolated cardiomyocytes are obtained from mouse hearts by retrograde collagenase perfusion. Rhod-shaped calcium tolerant cardiomyocytes are selected by differential centrifugation and albumin gradient and are plated on laminin-coated glass bottom coverslips (for confocal studies) or on 4% fetal calf serum pretreated multiwell dishes. To simulate IR in cardiomyocytes, two independent approaches are used: anoxic workstation under controlled atmosphere of 0% O2-5% H2 at 37° C. (Invivo2 Workstation Ruskinn, Bridgend, UK) and microscope-adapted microperfusion chamber (RC-43C/BS4 64-0371 Harvard Apparatus, Holliston, Mass., USA). For the anoxic workstation, cardiomyocytes are plated in 96-wells dishes, placed within the anoxic atmosphere and incubated for 15 min with glucose-free acidic ischaemic buffer (previously deoxygenated in an autoclave and bubbled with N2 for 20 min) containing (in mmol/l): 140 NaCl, 3.6 KCl, 1.2 MgSO4, 1 CaCl2, 20 HEPES, pH 6.4, and supplemented with 4 μmol/l resazurin, 100 μmol/l ascorbic acid, 0.5 mmol/l dithionite and 100

U/ml superoxide dismutase. For reperfusion, ischaemic buffer is washed out and oxygenated, glucose-containing control buffer (pH 7.4) is added for 10 min. To simulate ischaemia in the microperfusion chamber, laminin-attached cardiomyocytes placed on the stage of an inverted microscope are superfused, with the aid of a peristaltic pump, within a closed microperfusion chamber with ischaemic buffer (see above) at pH 6.4, continuously bubbled with N2 for 15 min. Reoxygenation is induced by switching to oxygenated, glucose-containing control superfusion, at pH 7.4. Distribution in the size of the nuclei and number of cardiomyocytes alive 24 hours after ischemia were used as outcome parameters. Treatment with GA is expected to lead to increased number of cardiomyocytes alive 24 hours after ischemia compared to controls.

Model of Limb Ischemia:

In vivo model of limb ischemia: Mice are submitted to unilateral femoral ligatures for a few hours (4-5) to a few days. Glycolic acid or vehicle are injected systemically when the ligatures are removed. Alternatively, glycolic acid is given before ligation systemically. Ischemia is confirmed by clinical scores (tissue and functional damages by gait analysis) and methoxyisobutylisonitrile (MIBI) scintigraphies at different days 0, 4, 6, 10, 20, and 30. Histological analysis is also performed to determine the extension of the ischemia. Glycolic acid is expected to reduce the extension of the ischemia and cell death.

Model of Intestinal Ischemia:

Rabbits are anesthetized with 3% barbital, 30-35 mg/intravenous injections. The small intestine is reflected to the left of the abdominal incision and then the SMA and SMV are identified. Mesenteric ischemia is confirmed when the mesenteric pulsation is lost and the intestine becomes pale. Ligation is maintained for 2, 4 and 6 hours. Upon removal of the ligation, the animal is injected intraarterially at the point of the ligature with either vehicle or glycolic acid to a final concentration in the tissue as the mentioned above. Alternatively, glycolic acid can be administered systemically before ligation. After removing the ligation, the animal is led free for 1 and 3 days and then is intracardially perfused. Intestinal samples are embedded in paraffin and sections are stained with a nuclear staining. Nuclear size distribution is analysed in different ischemic areas and compared to that of non-ischemic areas. Glycolic acid is expected to reduce the number of apoptotic nuclei and the ischemic areas.

Example 2

Experimental Results

The results show that in this in vitro ischemia model, ischemia induces a shift in the size of the nuclei to smaller nuclei as seen in apoptosis (see FIG. 1 and FIG. 2). This shift is partially reversed both by 4 days pretreatment with 5 mM glycolic acid (see FIG. 3) or by treating the neurons with 10 and 20 mM glycolic acid (see FIGS. 4 and 5) during reperfusion, leading to less apoptotic nuclei (nuclear size<30 µm2) and up to 65% more normal size nuclei (nuclear surface >30 µm2) 24 hours after ischemia when compared to control neurons that underwent ischemia without any treatment. This protective effect depends on the degree of ischemia and reaches 100% rescue in penumbra conditions.

Additionally, the number of cortical neurons alive 24 hours after ischemia was also counted. When applying 10 mM and 20 mM glycolic acid in penumbra like conditions, the number of neurons that survived ischemia was similar to the number of neurons observed in normoxia (see FIG. 6). Thus, suggesting that in penumbra conditions glycolic acid was able to rescue all neurons.

Interestingly, even in normoxia conditions it was observed that pretreatment with 2.5 mM and 5 mM glycolic acid protects neurons against the adverse conditions inherent to an in vitro setting.

The effect of lower concentrations of glycolic acid was tested when administered during reperfusion and an extra administration time (1 hour after reperfusion). The results show that 5 mM GA given during reperfusion is enough to rescue the effect of the ischemia on mouse cortical neurons (FIG. 7). Lower concentrations of glycolic acid given during reperfusion did not increase survival (data not shown) but decreased the concentration of LDH in the media (see below).

Finally, in order to test whether glycolic acid was reducing necrosis or apoptosis (programed cell death more important in the penumbra), the increase in Lactate dehydrogenase (LDH) concentration was controlled in the media 24 hours after ischemia. LDH is released by the cells during cell death. Increases in LDH concentration during the first 24 hours after ischemia are due to necrotic processes and apoptotic events. The results shows that the addition of 2,5 mM and 5 mM of glycolic acid during reperfusion are sufficient to decrease the concentration of LDH significantly ($p<0.05$) when compared to controls 24 hours after the ischemic insult (FIG. 8). This effect is observed only in ischemia, as we did not observe any difference between treatments in normoxia (FIG. 9), which also speaks against any toxicity of glycolic acid on the neurons at these concentrations.

CONCLUSIONS

These results show that glycolic acid protects neurons from ischemia. This protection is achieved both as a pretreatment and when glycolic acid is administered during reperfusion. This has important clinical implications, not only in stroke but potentially also for patients suffering a heart attack, or other ischemic diseases. The fact that glycolic acid is able to protect from ischemia even when administered during reperfusion makes it an ideal candidate to treat patients during the acute phase. In the clinic, the main treatments for stroke are the mechanical recanalization and the fibrinolysis. The administration of glycolic acid during these procedures has the potential to reduce the size of the stroke by protecting the core and the penumbra, therefore leading to an improved functional outcome.

REFERENCES

1. Leys D, Henon H, Mackowiak-Cordoliani M A, Pasquier F: Poststroke dementia. *Lancet Neurol* 2005, 4(11):752-759.
2. Freeman W D, Dawson S B, Flemming K D: The ABC's of stroke complications. *Semin Neurol,* 30(5): 501-510.
3. Love S: Oxidative stress in brain ischemia. *Brain Pathol* 1999, 9(1):119-131.
4. del Zoppo G, Ginis I, Hallenbeck J M, Iadecola C, Wang X, Feuerstein G Z: Inflammation and stroke: putative role for cytokines, adhesion molecules and NOS in brain response to ischemia. *Brain Pathol* 2000, 10(1):95-112.

5. Ishibashi N, Prokopenko O, Reuhl K R, Mirochnitchenko O: Inflammatory response and glutathione peroxidase in a model of stroke. *J Immunol* 2002, 168(4): 1926-1933.
6. Paravicini T M, Drummond G R, Sobey C G: Reactive oxygen species in the cerebral circulation: physiological roles and therapeutic implications for hypertension and stroke. *Drugs* 2004, 64(19):2143-2157.
7. Janssen A W M, de Leeuw F E, Janssen M C H: Risk factors for ischemic stroke and transient ischemic attack in patients under age 50. *Journal of Thrombosis and Thrombolysis* 2011, 31(1):85-91.
8. Lindsberg P J, Grau A J: Inflammation and Infections as Risk Factors for Ischemic Stroke. *Stroke* 2003, 34(10):2518.
9. Anand S S, Islam S, Rosengren A, Franzosi M G, Steyn K, Yusufali A H, Keltai M, Diaz R, Rangarajan S, Yusuf S: Risk factors for myocardial infarction in women and men: insights from the INTERHEART study. *European Heart Journal* 2008, 29(7):932.
10. Fowkes F G R, Rudan D, Rudan I, Aboyans V, Denenberg J O, McDermott M M, Norman P E, Sampson U K A, Williams L J, Mensah G A et al: Comparison of global estimates of prevalence and risk factors for peripheral artery disease in 2000 and 2010: a systematic review and analysis. *The Lancet*, 382(9901): 1329-1340.
11. Stone J R, Wilkins L R: Acute Mesenteric Ischemia. *Techniques in Vascular & Interventional Radiology*, 18(1):24-30.
12. Andersen F A: Final Report On the Safety Assessment of Glycolic Acid, Ammonium, Calcium, Potassium, and Sodium Glycolates, Methyl, Ethyl, Propyl, and Butyl Glycolates, and Lactic Acid, Ammonium, Calcium, Potassium, Sodium, and Tea-Lactates, Methyl, Ethyl, Isopropyl, and Butyl Lactates, and Lauryl, Myristyl, and Cetyl Lactates. *International Journal of Toxicology* 1998, 17(1 suppl):1-241.
13. W. WKaF: Synthesis of piperidyl (2)-glycolic acid ethyl ester. *Arch Pharm Ber Dtsch Pharm Ges* 1971, 4(304):248-253.
14. ROBBA M M R: Beta-Substituted Thiophene derivates. I. amino esters of (3-thienyl)-glycolic acids. *Ann Pharm Fr* 1965, 23:103-111.
15. ZYMALKOWSKI F S W: Preparation of various pyridyl- and quinolyl glycolic acid esters. *Arch Pharm Ber Dtsch Pharm Ges* 1957, 6(290/62):267-273.
16. Castillo X, Rosafio K, Wyss M T, Drandarov K, Buck A, Pellerin L, Weber B, Hirt L: A Probable Dual Mode of Action for Both L- and D-Lactate Neuroprotection in Cerebral Ischemia. *Journal of Cerebral Blood Flow & Metabolism* 2015, 35(10):1561-1569.
17. Campos F, Sobrino T, Ramos-Cabrer P, Argibay B, Agulla J, Perez-Mato M, Rodriguez-Gonzalez R, Brea D, Castillo J: Neuroprotection by glutamate oxaloacetate transaminase in ischemic stroke: An experimental study. *Journal of Cerebral Blood Flow & Metabolism* 2011, 31(6):1378-1386.
18. Maniskas M E, Roberts J M, Aron I, Fraser J F, Bix G J: Stroke neuroprotection revisited: Intra-arterial verapamil is profoundly neuroprotective in experimental acute ischemic stroke. *Journal of Cerebral Blood Flow & Metabolism* 2016, 36(4):721-730.
19. Wang H, James M L, Venkatraman T N, Wilson L J, Lyuboslaysky P, Myers S J, Lascola C D, Laskowitz D T: pH-Sensitive NMDA Inhibitors Improve Outcome in a Murine Model of SAH. *Neurocritical Care* 2014, 20(1):119-131.
20. Chan F K-M, Moriwaki K, De Rosa M J: Detection of Necrosis by Release of Lactate Dehydrogenase (LDH) Activity. *Methods in molecular biology* (Clifton, N.J.) 2013, 979:65-70.

The invention claimed is:

1. A method for the treatment of ischemic insults, comprising administering glycolic acid or a pharmaceutically acceptable salt or ester thereof, wherein said ester of glycolic acid is cleaved in vivo to release glycolic acid, by parenteral or oral administration, during reperfusion of ischemic tissue in a subject.

2. The method of claim 1, wherein the ischemic insult is associated with lack of blood or oxygen supply to a bodily tissue of a subject.

3. The method of claim 1, wherein the ischemic disease is characterised by increased necrosis with apoptosis in the affected hypoxic tissue in comparison to oxygenated tissue.

4. The method of claim 1, wherein the ischemic insult is cerebral ischemia.

5. The method of claim 1, wherein the ischemic insult is myocardial ischemia.

6. The method of claim 1, wherein the ischemic insult is peripheral limb disease.

7. The method of claim 1, wherein the ischemic insult is an acute ischemic injury.

8. The method of claim 1, wherein the ischemic insult is a human ischemic insult, or wherein the ischemic insult is ischemic insult of a production animal, mammalian domestic animal, zoo mammal or an endangered mammal.

9. The method of claim 1, wherein glycolic acid or a pharmaceutically acceptable salt or ester thereof is administered at least at a concentration of 2.5 mM.

10. The method of claim 1, wherein glycolic acid or a pharmaceutically acceptable salt or ester thereof is administered or used at least in amounts of about 10 µg/2 million cortical neurons to 5000 µg/2 million cortical neurons.

* * * * *